(12) United States Patent
Woodward et al.

(10) Patent No.: US 8,398,835 B2
(45) Date of Patent: Mar. 19, 2013

(54) UNITARY IONIC PROBE

(75) Inventors: John Robert Woodward, Windsor, CO (US); Pierre Antoine Robert Livrozet, Caluire et Cuire (FR); Jean-Francois Maurice Rene Schvan, Genay (FR); Russell Martin Young, Fort Collins, CO (US)

(73) Assignee: Hach Company, Loveland, CO (US)

( * ) Notice: Subject to any disclaimer, the term of this patent is extended or adjusted under 35 U.S.C. 154(b) by 1102 days.

(21) Appl. No.: 12/247,727

(22) Filed: Oct. 8, 2008

(65) Prior Publication Data

US 2009/0032396 A1 Feb. 5, 2009

Related U.S. Application Data

(63) Continuation-in-part of application No. 11/516,186, filed on Sep. 6, 2006.

(60) Provisional application No. 60/981,847, filed on Oct. 23, 2007.

(51) Int. Cl.
*G01N 27/26* (2006.01)

(52) U.S. Cl. .......................... 204/400; 204/420; 204/433

(58) Field of Classification Search .................. 204/400, 204/420, 433
See application file for complete search history.

(56) References Cited

U.S. PATENT DOCUMENTS

| | | | |
|---|---|---|---|
| 4,162,211 A * | 7/1979 | Jerrold-Jones | 204/420 |
| 4,196,383 A | 4/1980 | Teass, Jr. | |
| 4,440,619 A | 4/1984 | Daroczy et al. | |
| 4,650,562 A | 3/1987 | Harmon, III et al. | |
| 5,158,083 A | 10/1992 | Sacristan et al. | |
| 6,068,744 A * | 5/2000 | Seto et al. | 204/419 |
| 6,395,158 B1 * | 5/2002 | King et al. | 204/420 |
| 6,398,931 B1 * | 6/2002 | Burchette et al. | 204/416 |
| 6,551,478 B1 | 4/2003 | Bielawski et al. | |
| 6,793,787 B1 * | 9/2004 | Hirshberg et al. | 204/416 |
| 7,182,847 B1 | 2/2007 | Millar et al. | |
| 2003/0178305 A1 * | 9/2003 | Catalano et al. | 204/433 |
| 2005/0006237 A1 * | 1/2005 | Larkin et al. | 204/416 |

FOREIGN PATENT DOCUMENTS

| | | |
|---|---|---|
| EP | 0709669 A | 5/1996 |
| GB | 2097539 A | 11/1982 |
| WO | WO-2007/109521 A | 9/2007 |
| WO | WO-2007/109560 A | 9/2007 |

* cited by examiner

*Primary Examiner* — Luan Van
*Assistant Examiner* — Steven Rosenwald
(74) *Attorney, Agent, or Firm* — Ference & Associates LLC (57) ABSTRACT

A unitary ionic probe is provided. The unitary ionic probe includes a substantially elongate body including a central axis (AA), a proximal end, and a distal end. The unitary ionic probe further includes an active ion sensitive region that is located on and bonded into an exterior of the elongate body in a region of the proximal end and an active electrode in ionic communication with the active ion sensitive region. The unitary ionic probe further includes a reference ion sensitive region that is located on and bonded into the exterior of the elongate body and is spaced-apart from the active ion sensitive region and a reference electrode in ionic communication with the reference ion sensitive region.

38 Claims, 12 Drawing Sheets

UNITARY IONIC PROBE

RELATED APPLICATIONS

This application is a continuation-in-part of U.S. patent application Ser. No. 11/516,186, filed on Sep. 6, 2006, and entitled "Differential pH probe," and claims a common filing date for material in common with this application. This application claims benefit of, and priority from, U.S. provisional patent application No. 60/981,847, filed on Oct. 23, 2007, and entitled "Unitary Ionic Probe". The provisional is herein incorporated by reference.

BACKGROUND OF THE INVENTION

1. Field of the Invention

The invention is related to the field of an ionic probe.

2. Statement of the Problem

A measure of the ionic concentration of a fluid is desirable in many situations, including testing of fluids in manufacturing settings, for pharmaceutical production, food processing and/or food quality, water quality testing, etc. Measurement of an ionic level or activity can indicate completion of a reaction, indicate fractions of components, etc.

One measure can comprise a measure of a pH value, which comprises a measure of acidity of the fluid being tested. The pH measurement can indicate the acidic or basic condition or level of the fluid.

A pH measurement comprises a measurement of hydrogen ions in a solution, expressed as a logarithmic number between about zero and fourteen (sometimes extending into negative numbers for exceedingly acidic solutions). On the pH scale, a very acidic solution has a low pH value, such as zero or one, corresponding to a large concentration of hydrogen ions ($H^+$). In contrast, a very basic solution has a high pH value, corresponding to a very small number of hydrogen ions (or to a correspondingly large number of $OH^-$ ions). A neutral solution, such as substantially pure water, has a pH value of about seven.

A pH measurement probe typically includes an active electrode unit and a reference electrode unit. The active electrode unit comprises a glass tube with an ion sensitive glass bulb at one end. The tube contains an electrolyte and an active electrode. The reference electrode unit can likewise comprise a glass tube with an ion sensitive glass bulb at one end, an electrolyte, and a reference electrode.

For each of the electrode units, the hydrated layer of glass on the exterior of the ion sensitive bulb exchanges hydrogen ions with the fluid to be tested. This produces a charge in the hydrated layer on the outside of the bulb. The internal electrolyte interacts with the ion sensitive glass and reflects a voltage potential developed in the hydrated layer of the glass due to the constant ion concentration of the electrolyte inside the glass envelope. Therefore, the voltage potential across the glass membrane is the result of the difference between the inner and outer electrical charges.

The reference buffer solution is in ionic communication with the external fluid being tested. A potential difference (i.e., voltage) between the active and reference glass electrodes is thereby formed, similar to a battery. The voltage potential between the electrodes is directly related to the ion concentration of the solution. The reference electrode provides a stable potential against which the measuring electrode can be compared. The voltage potential can be processed according to a table, formula, or other algorithm to arrive at an ionic concentration measurement, such as a pH value, for example.

The accuracy of ionic and/or pH measurements can be affected by various factors, including temperature and/or improper or contaminated electrolyte solutions, for example. A common source of inaccuracy can be an improper or inaccurate reference signal generated from a reference electrode. If the reference signal is inaccurate, the resulting pH or ion measurement will be affected. Consequently, it is of great importance that a proper and accurate reference value be obtained.

SUMMARY OF THE INVENTION

A unitary ionic probe is provided according to the invention. The unitary ionic probe comprises a substantially elongate body including a central axis (AA), a proximal end, and a distal end. The unitary ionic probe further includes an active ion sensitive region that is located on and bonded into an exterior of the elongate body in a region of the proximal end and an active electrode in ionic communication with the active ion sensitive region. The unitary ionic probe further includes a reference ion sensitive region that is located on and bonded into the exterior of the elongate body and is spaced-apart from the active ion sensitive region and a reference electrode in ionic communication with the reference ion sensitive region.

A unitary ionic probe is provided according to the invention. The unitary ionic probe comprises a substantially elongate body including a central axis (AA), a proximal end, and a distal end. The unitary ionic probe further comprises an active ion sensitive region that is located on and bonded into an exterior of the elongate body in a region of the proximal end, wherein the active ion sensitive region extends substantially radially from the proximal end, and an active electrode in ionic communication with the active ion sensitive region. The unitary ionic probe further comprises a reference ion sensitive region that is located on and bonded into a circumferential outer surface and is spaced-apart from the active ion sensitive region and a reference electrode in ionic communication with the reference ion sensitive region.

A unitary ionic probe is provided according to the invention. The unitary ionic probe comprises a substantially elongate body including a central axis (AA), a proximal end, and a distal end. The unitary ionic probe further comprises an active ion sensitive region that is located on and bonded into a circumferential outer surface of the elongate body at the proximal end and an active electrode in ionic communication with the active ion sensitive region. The unitary ionic probe further comprises a reference ion sensitive region that is located on and bonded into the circumferential outer surface and spaced-apart from the active ion sensitive region and a reference electrode in ionic communication with the reference ion sensitive region.

A unitary ionic probe is provided according to the invention. The unitary ionic probe comprises a substantially elongate body including a central axis (AA), a proximal end, and a distal end. The elongate body is substantially cylindrical. The unitary ionic probe further comprises an active ion sensitive region bonded into an exterior of the elongate body in a region of the proximal end and an active electrode in ionic communication with the active ion sensitive region. The unitary ionic probe further comprises a reference ion sensitive region bonded into the exterior of the elongate body and spaced-apart from the active ion sensitive region and a reference electrode in ionic communication with the reference ion sensitive region. The unitary ionic probe further comprises an inner wall forming a reference chamber located at the distal end. The reference chamber holds the reference electrode and is in communication with the reference ion sensitive region.

DESCRIPTION OF THE DRAWINGS

The same reference number represents the same element on all drawings. It should be understood that the drawings are not necessarily to scale.

DETAILED DESCRIPTION OF THE INVENTION

FIGS. 1-12 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
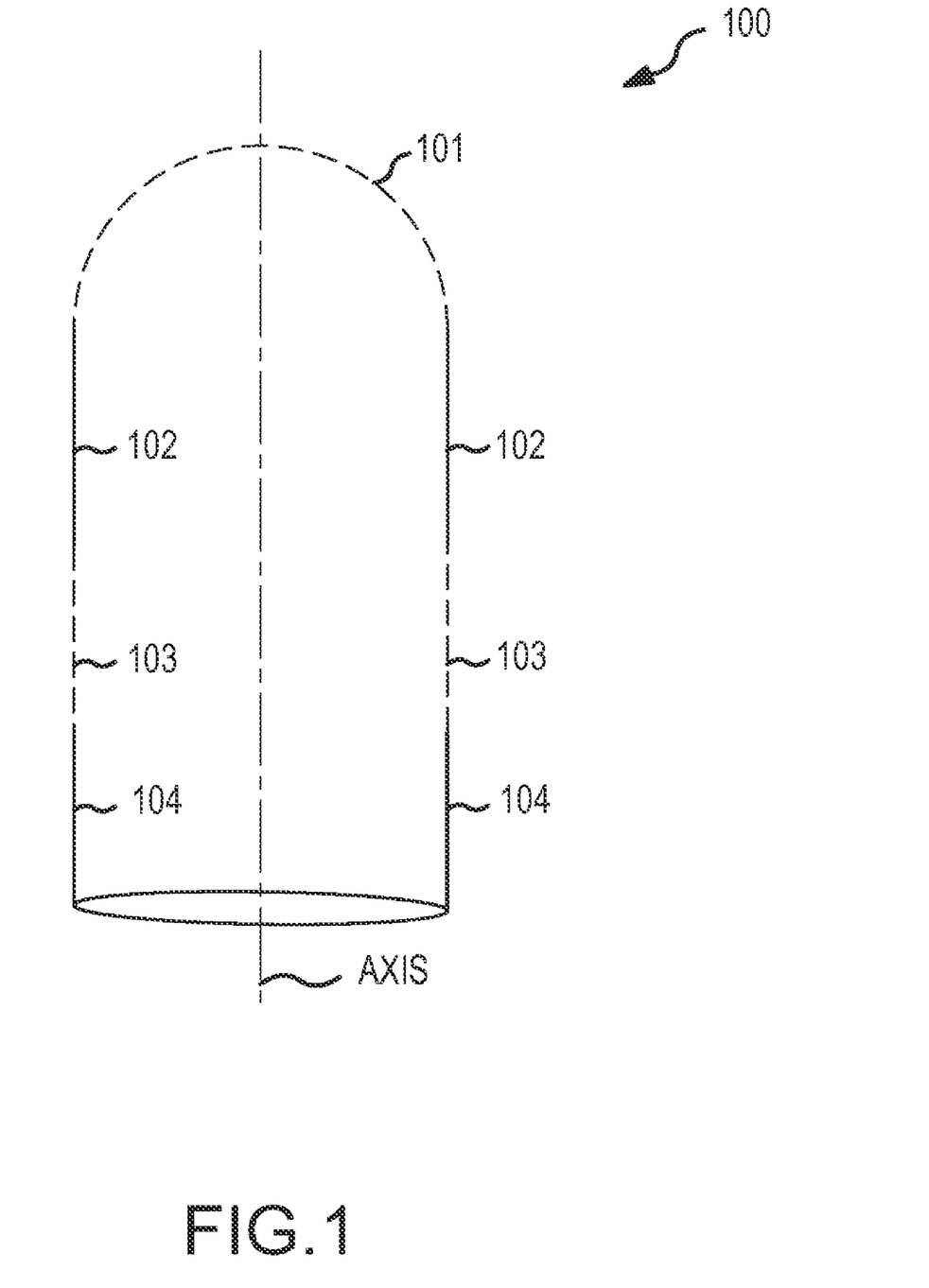
FIG. 1 illustrates glass piece used in differential pH probe, in an example embodiment of the invention.

FIG. 1 illustrates glass piece 100 used in differential pH probe 150 (shown in FIG. 4), in an example embodiment of the invention. Glass piece 100 is depicted as a tube, although other suitable shapes could be used. A generalized cylinder is a cylinder where the cross section can be any shape. Glass piece 100 includes active areas 101 and 103, in addition to non-active areas 102 and 104. Active areas 101 and 103 are formed of pH sensitive glass. An example of pH-sensitive glass is lithium-ion conductive glass. Non-active areas 102 and 104 are formed by non-pH sensitive glass. Note that alternative materials other than glass could be used for piece 100, such as pH-sensitive polymers and plastics.

Note that both the active and non-active areas are integrated together to form a single piece of glass—glass piece 100. This integration could be accomplished by treating a single glass tube to form the active and non-active areas. Alternatively, the active and non-active areas could be formed separately from one another and then fused together to form glass piece 100.

Note that active areas 101 and 103 share the same axis, making them co-axial with one another. The co-axial configuration allows for a large active area 101 while reducing the overall size of the probe 150. The single piece configuration provides structural strength and requires fewer seals than a multiple piece configuration.

Figure 2:
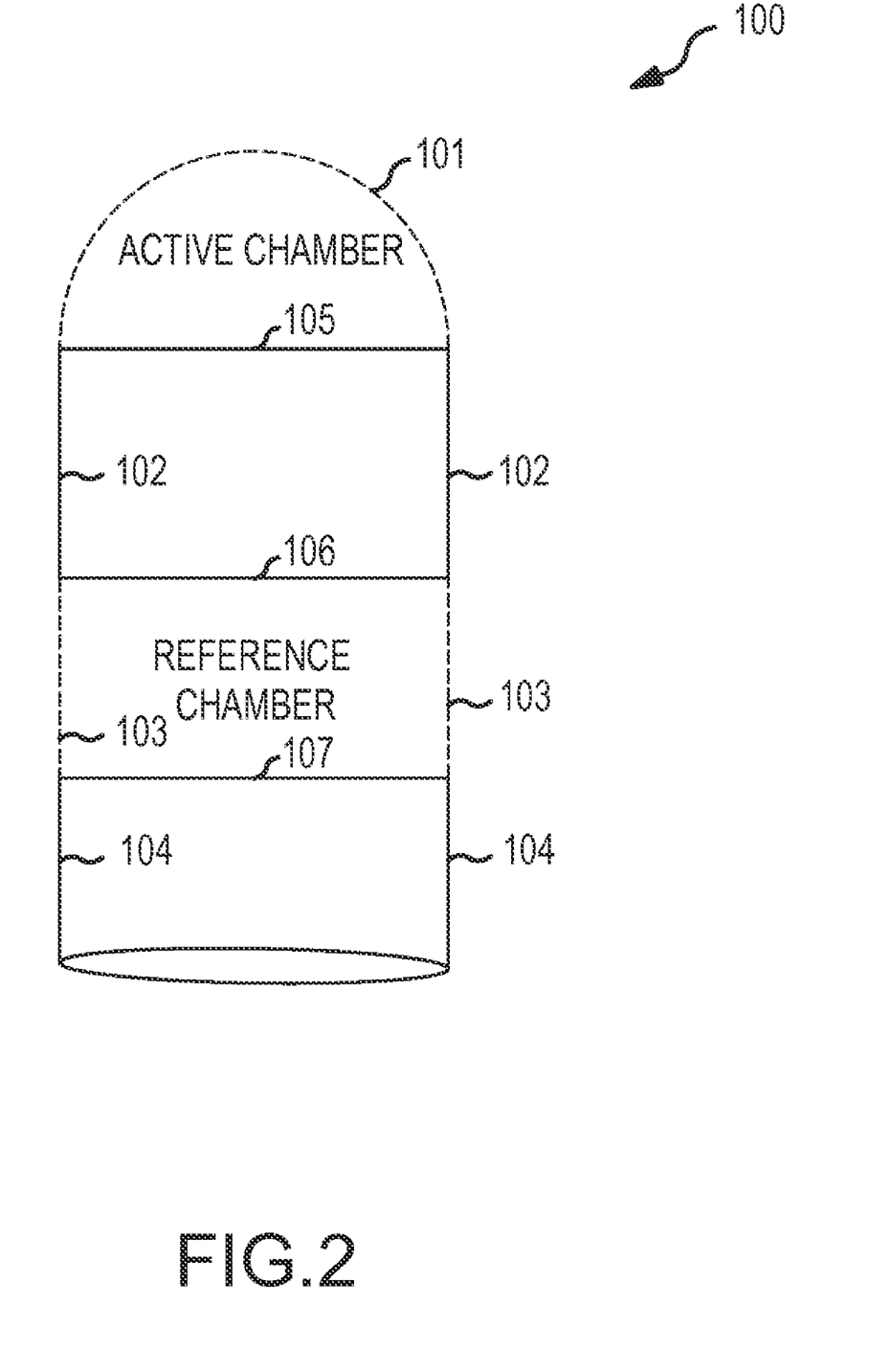
FIG. 2 illustrates glass piece with seals, in an example embodiment of the invention.

FIG. 2 illustrates glass piece 100 from FIG. 1, in an example embodiment of the invention. Glass piece 100 now has seals 105, 106, and 107. Seals 105-107 could be rubber, silicon, or some other suitable insulating material. Active area 101 and seal 105 form a first chamber, referred to as the active chamber. Active area 103 and seals 106-107 form a second chamber, referred to as the reference chamber. Both the active and reference chambers are filled with an electrolyte solution. In one example embodiment of the invention, glass piece 100 may be called a container that is divided into a number of different chambers.

Figure 3:
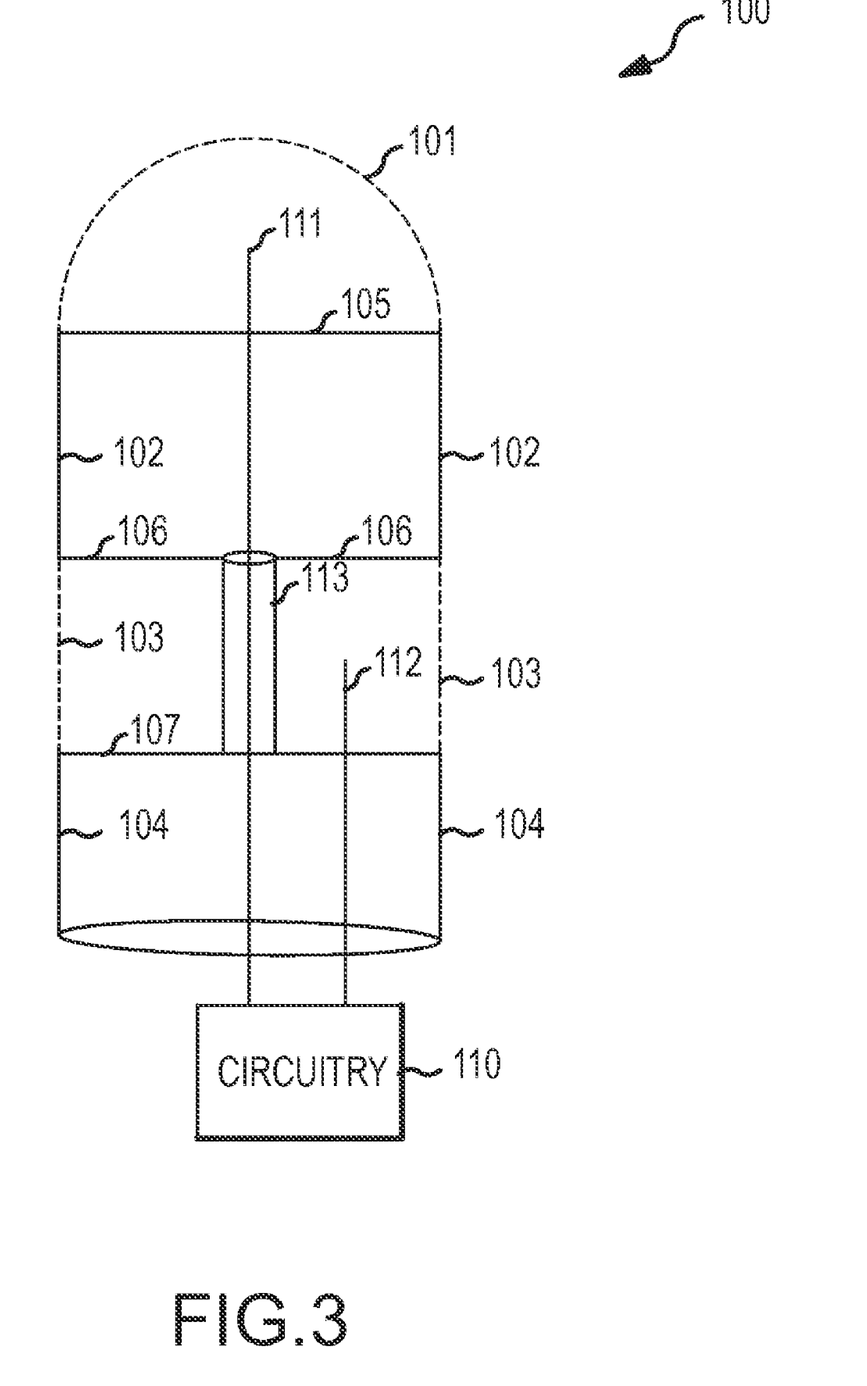
FIG. 3 illustrates glass piece with seals and circuitry, in an example embodiment of the invention.

FIG. 3 illustrates glass piece 100 from FIG. 2 and also shows circuitry 110. Glass piece 100 includes active electrode 111 that is exposed within the active chamber and then runs to circuitry 110. Note that insulating tube 113 is used so that active electrode 111 runs through the center of the reference chamber, but is not exposed within the reference chamber. Glass piece 100 also includes reference electrode 112 that is exposed within the reference chamber and then runs to circuitry 110.

Figure 4:
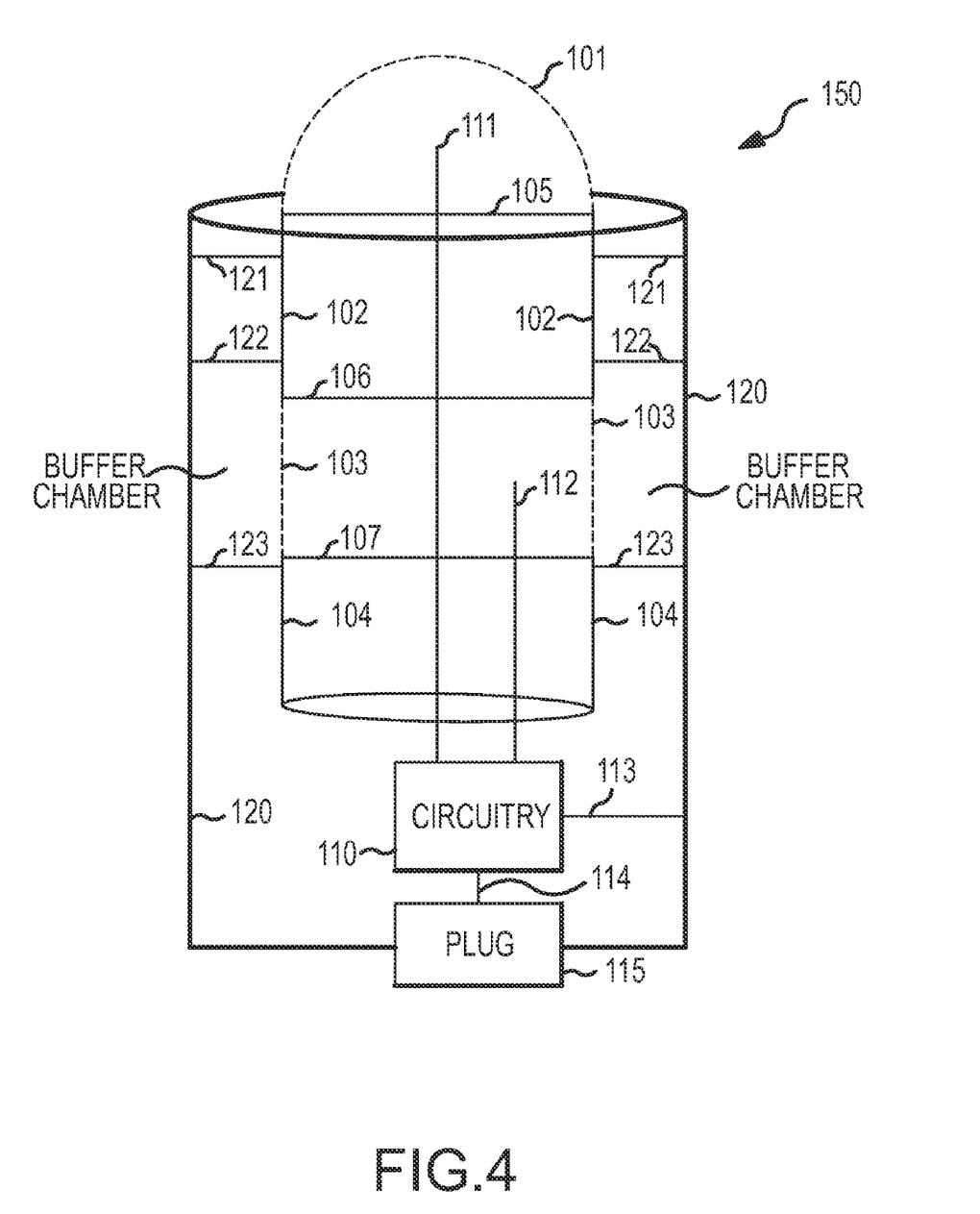
FIG. 4 illustrates differential pH probe, in an example embodiment of the invention.

FIG. 4 illustrates differential pH probe 150 in an example of the invention. Probe 150 includes glass piece 100 and circuitry 110 as described in FIGS. 1-3. Probe 150 also includes conductive enclosure 120. Conductive enclosure 120 could be tube-shaped like glass piece 100, although other shapes could be used. Glass piece 100 and circuitry 110 are placed within conductive enclosure 120.

Conductive enclosure 120 includes seals 121, 122, and 123. In this example with glass piece 100 and enclosure 120 being tube-shaped, seals 121-123 could be doughnut-shaped discs, although other shapes could be used in other examples. These disks could have much larger contact areas than conventional O-rings in order to provide better seals. Seals 121-123 could be rubber, silicon, or some other insulating material. Seals 121-122 provide a junction that allows electrical conductivity, but not fluid transfer, between the buffer chamber and the sample being tested. To provide this junction, seals 121-122 could be silicon disks with ceramic frits (tubes), where seals 121-122 are separated by a salt gel to form a salt bridge.

Seal 121 seals the end of enclosure 120 so that active area 101 of the active chamber may remain exposed to an external sample, but so that the external sample will not enter the enclosure 120. Enclosure 120, seals 122-123, and active area 103 form a buffer chamber around active area 103 of glass piece 100. This buffer chamber is filled with a buffer solution that maintains a constant pH—typically about seven.

Circuitry 110 is grounded to conductive enclosure 120 by electrical line 113. Circuitry 110 is coupled to plug 115 by electrical lines 114. Thus, circuitry 110 communicates with external systems through lines 114 and plug 115. In other embodiments, circuitry 110 may communicate with an external system using a wireless or non-contact technology, for example an optical link or an RF link.

In operation, active area 101 of probe 150 is dipped into the sample whose pH will be determined. Note that seal 121 prevents the sample from entering the enclosure 120. The sample (with unknown pH) interacts with active area 101 to produce a first voltage across active area 101. This first voltage is referred to as the active voltage and corresponds to the unknown pH of the sample. Active electrode 111 detects the active voltage and indicates the active voltage to circuitry 110.

In a similar manner, the buffer solution (with known pH) interacts with active area 103 to produce a second voltage across active area 103. This second voltage is referred to as the reference voltage and corresponds to the known pH of the buffer solution. Reference electrode 112 detects the reference voltage and indicates the reference voltage to circuitry 110.

Circuitry 110 processes the active and reference voltages in the conventional manner to determine the pH of the sample. Circuitry 110 indicates the pH of the sample to external systems (not shown) that are plugged into plug 115.

Conductive enclosure 120 is typically held by hand during testing. Note that conductive enclosure 120 electrically shields the internal components of probe 150 (i.e., the electrodes 111-112 and the circuitry 110) from hand capacitance. Conductive enclosure 120 also provides a ground. Note that conductive enclosure 120 could be stainless steel, aluminum, or some other conductive material. In one example embodiment of the invention, conductive enclosure 120 may have a conducting part and a non-conducting part. The conductive part would begin just below the seal 123 and would cover and shield the lower portion of the probe 150, including the circuitry 110. The upper portion starting just below the seal 123 would be made from a non-conductive material or have a non-conductive coating. When using the two part enclosure, a separate ground rod may be located in the outer salt bridge seal 121.

Figure 5:
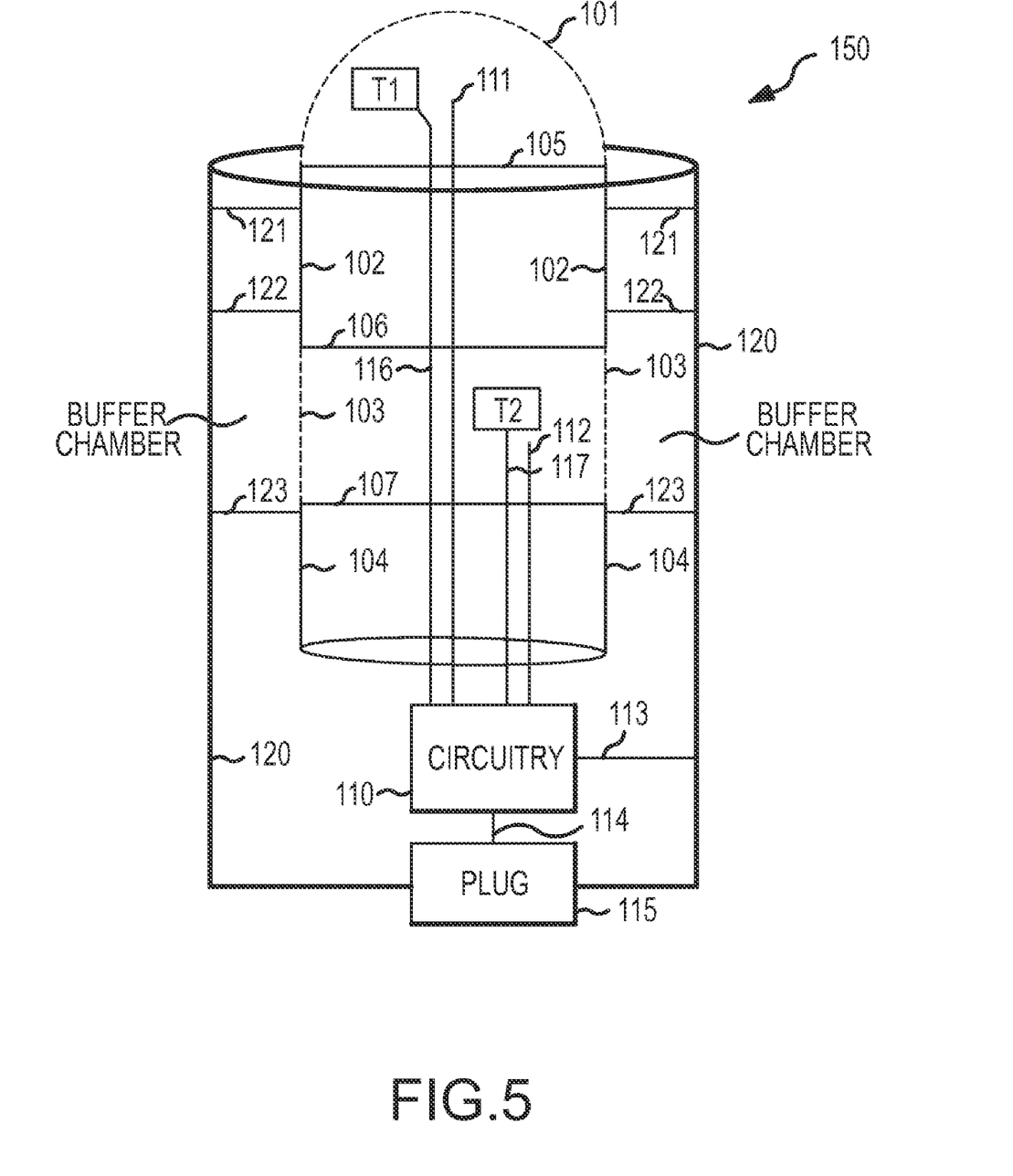
FIG. 5 illustrates differential pH probe with temperature sensors, in an example embodiment of the invention.

FIG. 5 illustrates differential pH probe 150 in an example of the invention. Thermistor T1 has been added to the active chamber to detect the temperature near the active electrode 111. Thermistor T2 has been added to the reference chamber to detect the temperature near the reference electrode 112. Thermistors T1 and T2 could be integrated within seals 105-107. Thermistor T1 transfers its temperature information to circuitry 110 over electrical line 116. Thermistor T2 transfers its temperature information to circuitry 110 over electrical line 117. Circuitry processes the temperature information from the thermistors T1 and T2 to provide temperature compensation during the pH determination. In another embodiment of the invention, the thermistor T1 may be located on the outside of the active chamber (not shown) and be exposed to the sample and used to detect the temperature of the sample. In another embodiment of the invention, the thermistor T2 may be located in the buffer chamber.

Figure 6:
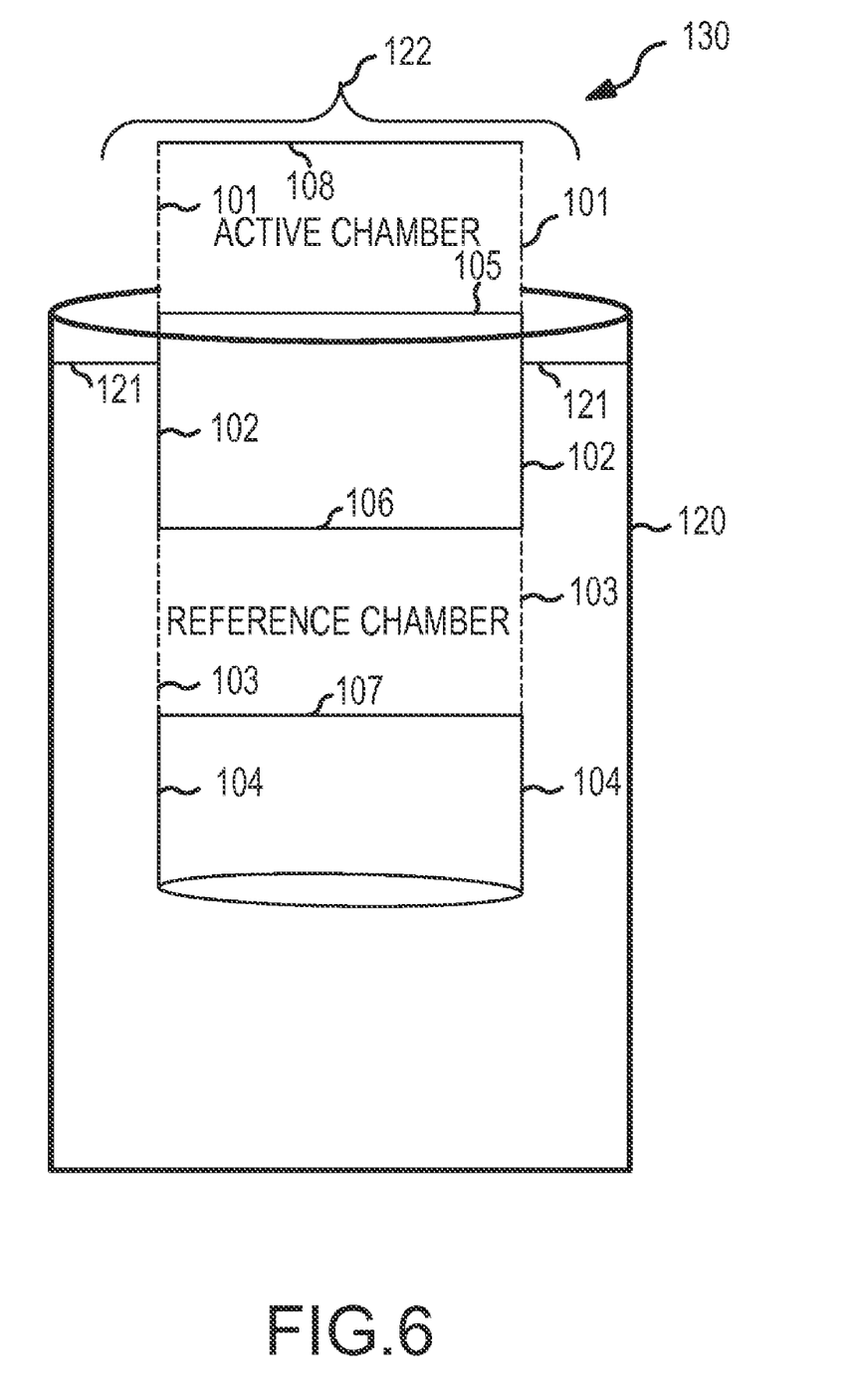
FIG. 6 illustrates glass piece used in a differential pH probe in an example embodiment of the invention.

FIG. 6 illustrates an alternative to glass piece 100. Note that some details from the previous figures are omitted for clarity. Glass piece 130 is now used for probe 150 instead of glass piece 100. Glass piece 130 is similar to the glass piece 100 with active areas 101 and 103 and non-active areas 102 and 104 separated by seals 105-107 to form the active and reference chambers. The variation from the glass piece 100 is in the shape of the active chamber. Active area 101 is no longer a dome at the top of the glass piece, but is now formed by the walls of glass piece 130 in the same way that active area 103 forms the reference chamber. Thus, the active chamber has the same geometry as the reference chamber. Non-active glass 108 is used at the top of the active chamber, although a seal could be used instead of non-active glass 108 if desired. The top of the active chamber is protected by cap 122. Cap 122 could be rubber, metal, or some other protective material that is adhered to glass piece 130.

Figure 7:
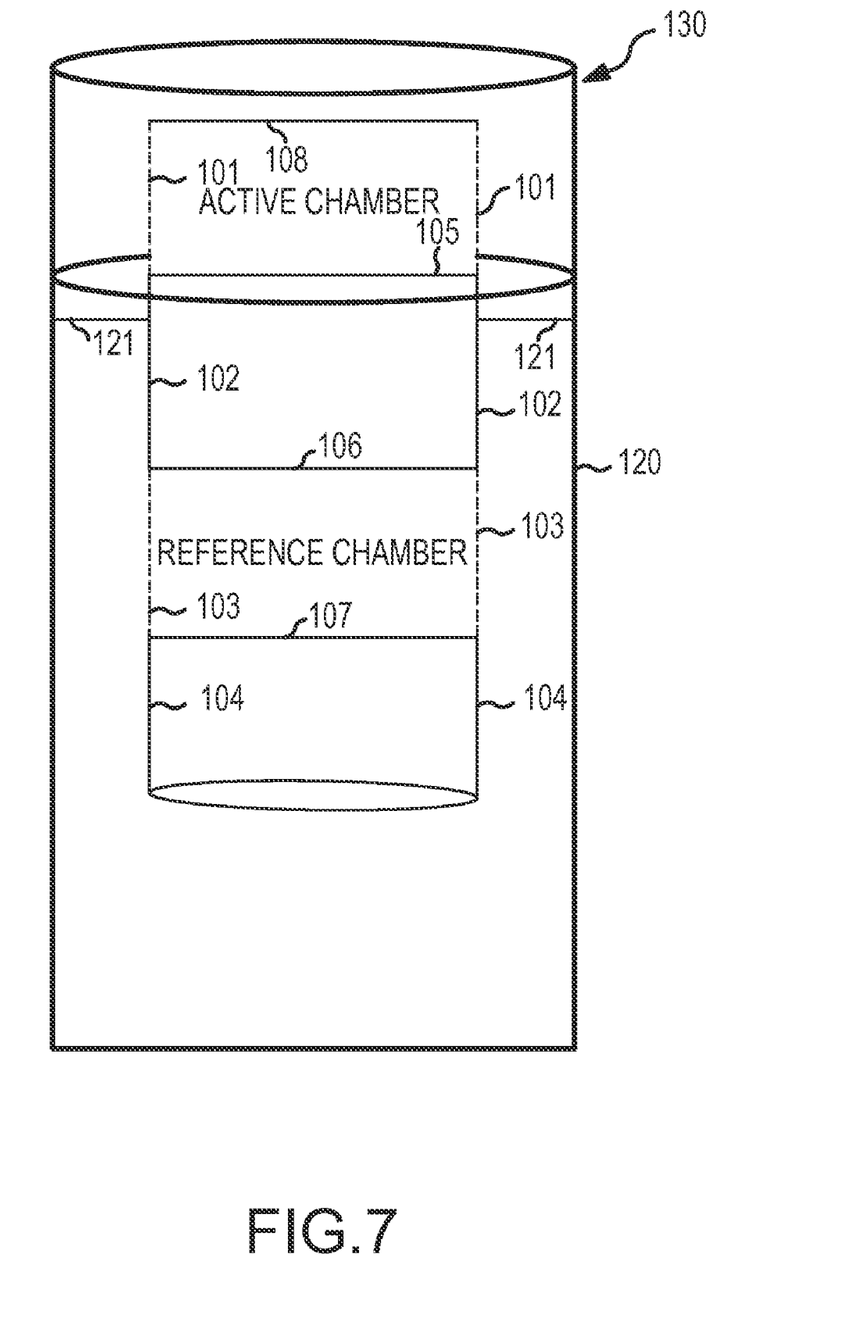
FIG. 7 illustrates a variation for conductive enclosure in another example embodiment of the invention.

FIG. 7 illustrates a variation for conductive enclosure 120. Note that some details from the previous figures are omitted for clarity. Glass piece 130 is used, but glass piece 100 could be used as well. Enclosure 120 now extends above the active chamber of glass piece 130 to provide protection. The extension of enclosure 120 must still allow the sample to contact the active area 101, so openings in the enclosure 120 should be provided for this purpose. The sample should still not be allowed to pass the seal 121.

Figure 8:
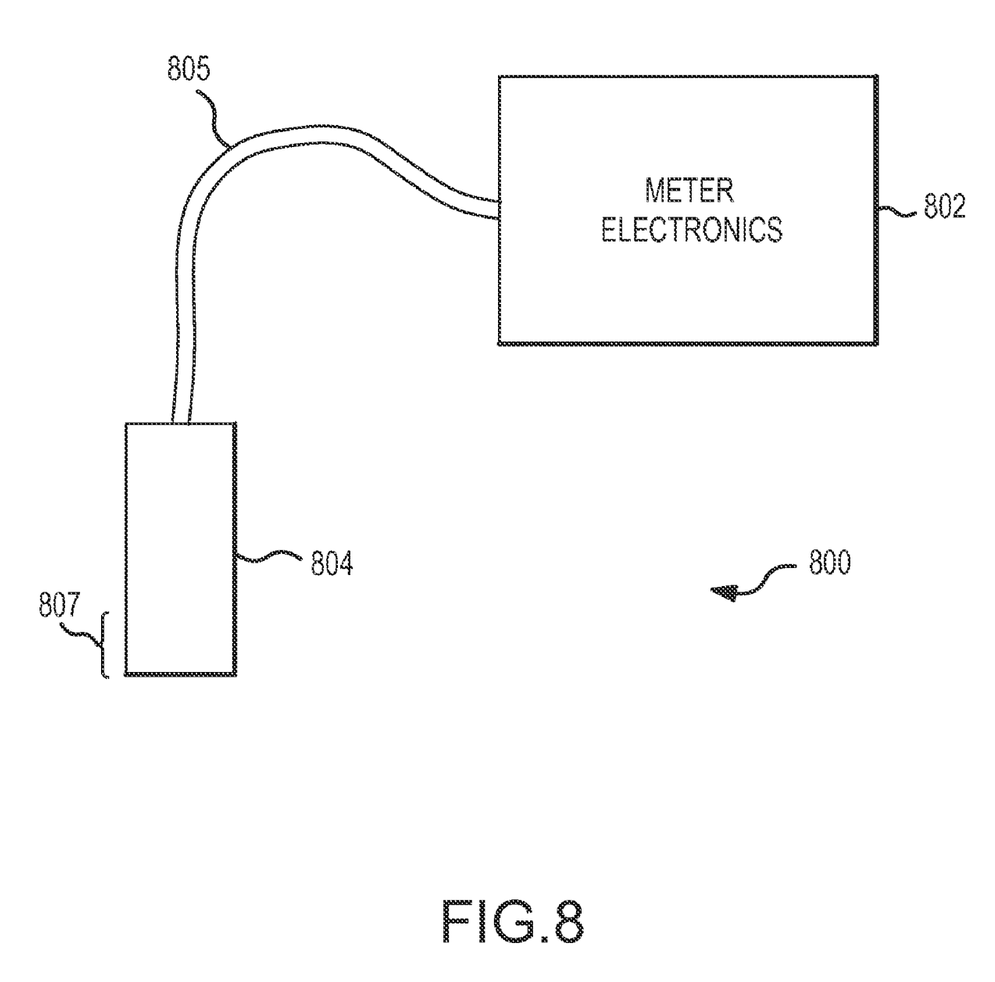
FIG. 8 shows an ion meter according to an embodiment of the invention.

FIG. 8 shows an ion meter 800 according to an embodiment of the invention. The ion meter 800 includes an ionic probe 804, meter electronics 802, and a cable 805 connecting the ionic probe 804 to the meter electronics 802. The ionic probe 804 can include a test end 807 and can include an active ion sensitive region 820 located at or near the test end 807.

In use, the ionic probe 804 is placed in an external test fluid. The test end 807 is contacted to or immersed in the external test fluid, although the entire ionic probe 804 can be immersed. The external test fluid can comprise water, for example, although it should be understood that various other fluids can be tested. To that end, the ionic probe 804 is immersed in and interacts with the sample fluid and generates a voltage signal that is transferred to the meter electronics 802 by the cable 805. The voltage signal generated by the ionic probe 804 is related to an ion level or ion concentration within the external test fluid.

The meter electronics 802 receives the voltage signal from the ionic probe 804 and processes the signal in order to obtain an ionic measurement, such as a pH value, for example. However, it should be understood that the ion meter 800 can detect and/or measure other ions and ion levels. The processing can include comparing the voltage signal to a reference signal, wherein the ionic measurement can be determined from a variation between a voltage level of the active voltage signal and a voltage level of the reference signal. Therefore, it is important that the reference signal be steady and continuous in order to serve as a basis for all ionic measurements. If the reference signal is not steady and constant, the resulting ionic measurement will be inaccurate.

In the prior art, a reference electrode has historically been constructed as a separate device, wherein a prior art ionic probe includes both an active electrode assembly and a reference electrode assembly, typically as sub-units.

The prior art reference electrode assembly typically comprises a bare reference electrode in an inner reference chamber. A salt bridge or other ionic interface enables ionic communication between the bare reference electrode in the inner chamber and one or more intervening chambers. This slows down and reduces the poisoning or clogging effects on the reference electrode, but does not eliminate them.

The major problem with a pH probe including a reference electrode in a reference chamber is in the junction between the internal reference solution and the external fluid, such as a salt bridge. The junction is vital to the function of the reference electrode and to the establishment of an ionic circuit. Clogging or failure of the junction usually leads to very slow and/or erroneous readings. The junction can also allow the contamination of the internal reference solution by the external test fluid. This poisons the prior art reference electrode, rendering it inaccurate. As a result, the prior art reference electrode commonly has to be replaced after a duration of use. Some manufacturers have attempted to overcome this problem by the employment of multiple junctions and chambers between the prior art reference electrode and the external test fluid. Others have used flowing junctions in which a continuous supply of reference solution is fed into the prior art reference electrode compartment and exits via a small hole or ground glass aperture. This continuous replacement operation prevents the contamination of the reference solution and therefore of the prior art reference electrode. However, it has the disadvantage of requiring additional expensive and complex apparatus for conducting and metering the solution into the prior art reference electrode chamber and requiring a supply of reference solution.

Figure 9:
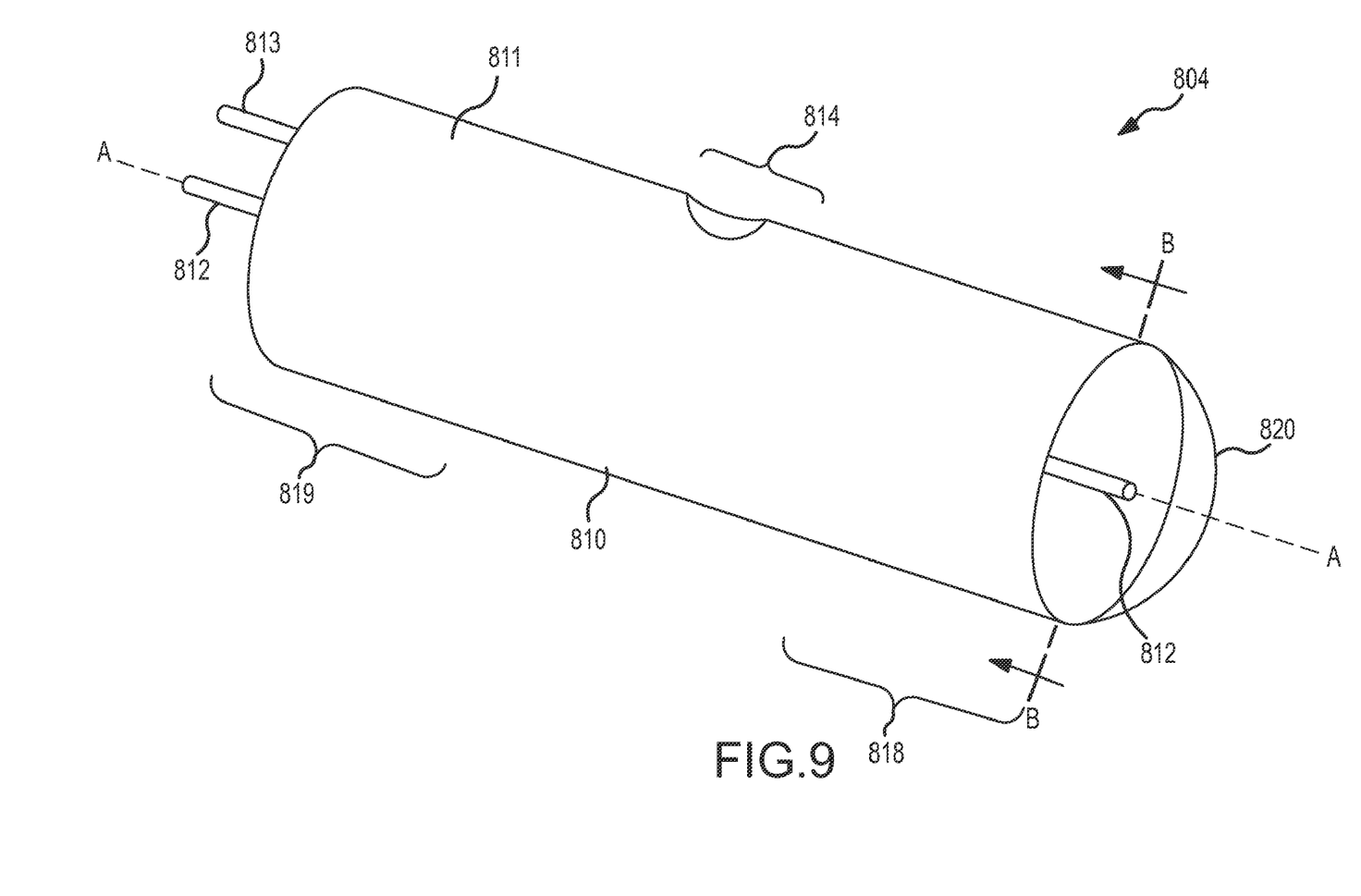
FIG. 9 shows a unitary ionic probe according to an embodiment of the invention.
Figure 10:
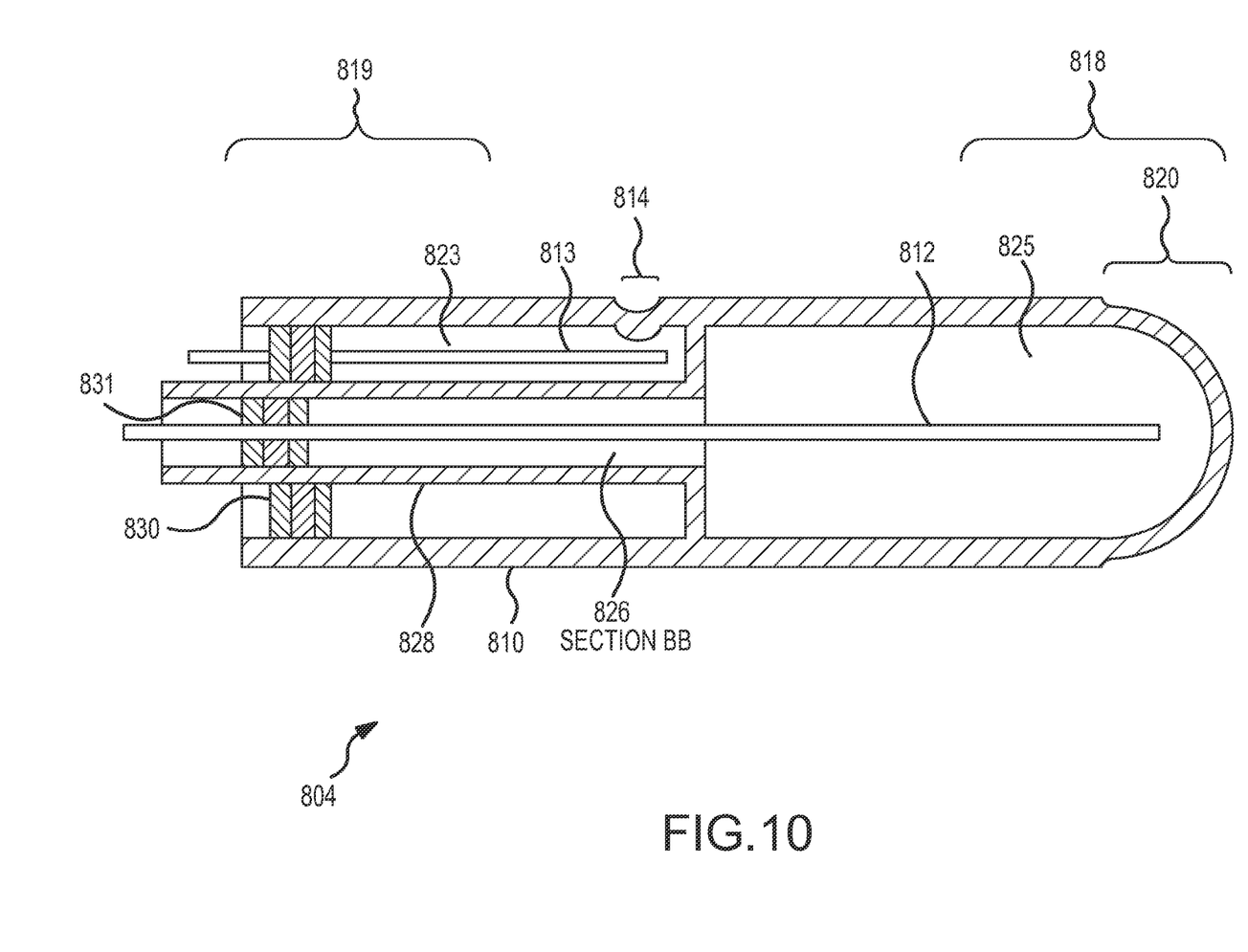
FIG. 10 is a longitudinal cross-sectional view BB of the ionic probe according to an embodiment of the invention.

However, the problem is overcome by encasing a reference electrode in a substantially ion-impermeable chamber, such as a glass chamber as shown in the construction in U.S. Pat. No. 6,395,158 to King et al. for use in differential pH probes. The reference electrode 813 is immersed in a reference solution held in the impermeable chamber and communicates with the external test fluid via a reference ion sensitive region 814, similar to that used for the active electrode. Because the reference electrode 813 is encapsulated in the impermeable chamber, there is less likelihood of poisoning and the pH value of the internal reference solution is kept substantially constant. As a result, the measured potential difference between the active electrode 812 and the reference electrode 813 is dependent only upon the ionic or pH value of the external test fluid being measured and the pH of the internal reference solution inside the reference chamber 823 and contacting the ion selective glass 814. As a result, the reference voltage remains essentially constant over time, regardless of the ionic level or content of the external test fluid, while completing a circuit between the reference electrode 813 and the active electrode 812. Consequently, an active voltage at the active electrode 812 can be compared to a reference voltage in order to determine a pH level or other ionic level.

FIG. 9 shows a unitary ionic probe 804 according to an embodiment of the invention. Components in common with other figures share reference numbers. The unitary ionic probe 804 includes a substantially elongate body 810 including a central axis AA, a proximal end 818, and a distal end 819. A circumferential outer surface 811 extends between the proximal end 818 and the distal end 819.

An active ion sensitive region 820 is located on and bonded into an exterior of the elongate body 810 in a region of the proximal end 818. The active ion sensitive region 820 is located at least partially at the proximal end 818 of the unitary ionic probe 804. In some embodiments, the active ion sensitive region 820 is located on and bonded into the proximal end 818 and extends substantially radially from the proximal end 818 (shown). Alternatively, in other embodiments the active ion sensitive region 820 is located on and bonded into the circumferential outer surface 811 (not shown).

The active ion sensitive region 820 can extend from the circumferential outer surface 811 (i.e., can be convex) or can be substantially flat or even concave in shape.

A reference ion sensitive region 814 is located on and bonded into an exterior of the elongate body 810 and spaced-apart from the active ion sensitive region 820. In some embodiments, the reference ion sensitive region 814 is located on and bonded into the circumferential outer surface 811. However, it should be understood that alternatively the placement of the active ion sensitive region 820 and the reference ion sensitive region 814 can be exchanged.

The active ion sensitive region 820 comprises a first portion of ion-sensitive material bonded into the elongate body 810 and the reference ion sensitive region 814 comprises a second portion of ion-sensitive material bonded into the elongate body 810. The first portion and the second portion can be substantially similar, such as sharing common pH transmissivity characteristics and/or transmissivity speeds. Alternatively, the first portion and the second portion can be different, depending on the desired characteristics of the ionic probe 804. The reference ion sensitive region 814 and the active ion sensitive region 820 do not have to be of the same size, shape, thickness, composition, etc. For example, the reference ion sensitive region 814 can comprise an ion sensitive material possessing a slower ion interaction speed as the reference electrode 813 is held in a non-changing solution. In contrast, the active ion sensitive region 820 may employ an ion sensitive material in order to achieve a voltage potential reading for different external test fluids.

The ionic probe 804 includes an active electrode 812 and a reference electrode 813. The electrodes 812 and 813 extend from the distal end 819 of the ionic probe 804 and may connect to or be attached to the cable 805 (see FIG. 8). Alternatively, the electrodes 812 and 813 can connect to some manner of internal circuit board or other component (not shown) that is in turn connected to the cable 805. The active electrode 812 is contained within the probe 804 and therefore is not in contact with the reference buffer solution.

The electrodes 812 and 813 can be formed of any suitable material. In some embodiments, the electrodes 812 and 813 can be formed of silver/silver chloride, as is known in the art. However, other materials are contemplated and are within the scope of the description and claims.

In some embodiments, the active electrode 812 is located substantially on the axis AA, as shown. However, it should be understood that other arrangements are contemplated and are within the scope of the description and claims.

The elongate body 810, and therefore the ionic probe 804 as a whole, can comprise a substantially cylindrical shape, as shown. However, it should be understood that the elongate body 810 and the ionic probe 804 can comprise any desired shape, including oval, rectangular, or even irregular in cross-section, for example.

The elongate body 810 (and an inner wall 828, see FIG. 10), can comprise any suitable material. The material must be substantially non-porous and must not permit fluid exchange between the interior and the exterior. In addition, the ion sensitive regions must be able to be affixed to the material. For example, in one embodiment the elongate body 810 is formed of glass. However, other materials are contemplated and are within the scope of the description and claims.

The active ion sensitive region 820 extends from the proximal end 818 of the ionic probe 804 and is designed to contact the external test fluid. The active electrode 812 resides in an active chamber 825 (see FIG. 10) located at least partially at the proximal end 818 of the elongate body 810. As a result, the active electrode 812 is adjacent to an inner surface of the active ion sensitive region 820 and is in ionic communication with the active ion sensitive region 820. A voltage potential is generated on the active electrode 812 as a result of ion interaction at the active ion sensitive region 820. The active ion sensitive region 820 and the reference ion sensitive region 814 form an ionic circuit, similar to a battery. It should be understood that it some or all of the ionic probe 804 may be immersed in the external test fluid, as previously noted.

The active ion sensitive region 820 allows ion exchange at the outer ion sensitive area of the electrode. There is a substantially constant charge on the inner surface of the ion sensitive material. This allows the development of a potential difference between an external test fluid and the active electrode 812. The magnitude of this potential is dependent on the ionic value of the solution, such as the pH value, for example. The same is true of the reference ion sensitive region 814.

The ion sensitive regions 814 and 820 can comprise any manner of ion transmissive material that does not permit a fluid exchange between the inside and the outside of the elongate body 810. For example, the ion sensitive regions 814 and 820 can be formed of an ion sensitive glass. The ion sensitive regions 814 and 820 can comprise a specially formulated pH sensitive lithium ion-conductive glass consisting of the oxides of silica, lithium, calcium, and other elements.

The structure of the pH glass allows ionic interaction between the solution to be measured (i.e., the external test fluid) and the hydrated layer of the glass. However, other materials are contemplated and are within the scope of the description and claims.

The ion sensitive regions 814 and 820 can comprise portions of the elongate body 810. The ion sensitive regions 814 and 820 can be located at any positions on the elongate body 810. The ion sensitive regions 814 and 820 can be molded or bonded into apertures in the elongate body 810, for example. Alternatively, the ion sensitive regions 814 and 820 can be formed in the elongate body 810 during its formation, such as by glass blowing, for example.

FIG. 10 is a longitudinal cross-sectional view BB of the ionic probe 804 according to an embodiment of the invention. Components in common with other figures share reference numbers. The cross-sectional view BB shows the internal components of the ionic probe 804. It can be seen that, in addition to the previously disclosed components, the ionic probe 804 includes an inner wall 828 dividing the interior volume of the elongate body 810 into a reference chamber 823 and an active chamber 825. The ionic probe 804 further comprises seals 830 and 831.

The seals 830 and 831 can comprise bodies formed of any suitable sealing material. The seals 830 and 831 can comprise a single device or material or can comprise multiple layers or devices. The seals 830 and 831 can be installed to or formed in the distal end 819 of the elongate body 810. The seals 830 and 831 block off the distal end 819 of the elongate body 810, forming and completing the active chamber 825 and forming and completing the reference chamber 823. In some embodiments, the active chamber 825 is located primarily in the proximal end 818 and the reference chamber is located primarily in the distal end 819. In some embodiments, the active chamber 825 includes a passage 826 that connects the active chamber 825 substantially to the distal end 819 of the elongate body 810. In the embodiment shown, the seal 830 blocks off the reference chamber 823 and the seal 831 blocks off the passage 826 and consequently the active chamber 825.

A portion of the active electrode 812 resides in the active chamber 825. The active chamber 825 further contains an active solution. The active solution comprises any manner of solution that can perform ion interaction between the active electrode 812 and the active ion sensitive region 820, such as an electrolyte solution, for example.

A portion of the reference electrode 813 resides in the reference chamber 823. The reference chamber 823 further contains a reference solution. The reference solution comprises any manner of solution that can perform ion interaction between the reference electrode 813 and the reference ion sensitive region 814, such as an electrolyte solution, for example.

The reference solution can be substantially the same or can differ in ionic level from the active solution. For example, the active solution can have a first pH value and the reference solution can be chosen to have a second pH value that differs from the first pH value.

In operation, ions interact with the active ion sensitive region 820 in order to create a voltage potential inside the active chamber 825 and on the active electrode 812. Likewise, ions can interact with the reference ion sensitive region 814 in order to create a voltage potential inside the reference chamber 823 and on the reference electrode 813. The charge on the external ion selective material forming the reference electrode unit is substantially constant. In contrast, the charge on the external surface of the ion selective material of the active electrode unit varies according to the ion concentration in the external test fluid. Therefore, the two electrode units can be used to detect and measure a resulting voltage difference, wherein the voltage difference is related to an ionic or pH level of the external test fluid. In use, the voltage potential between the active electrode 812 and the reference electrode 813 may be processed ratiometrically against a ground potential or ground signal.

The inner wall 828 in some embodiments is substantially coaxial/mono-axial with the axis AA of the elongate body 810. Consequently, the inner wall 828 in some embodiments forms an annular reference chamber 823 within the elongate body 810. However, it should be understood that the inner wall 828 can be formed in other configurations. For example, the reference chamber 823 can extend only partially around an inner volume of the elongate body 810 or can comprise a chamber formed of a portion of the cross-sectional shape of the elongate body 810.

The ionic probe according to some embodiments can provide a probe that requires fewer components. For example, the ionic probe according to the invention advantageously includes only a single seal. The ionic probe according to some embodiments therefore includes fewer avenues for leakage. The ionic probe according to some embodiments can provide a probe that features an easier manufacturing process requiring fewer components, fewer assembly steps, and less demanding tolerances (see FIG. 4). The ionic probe according to some embodiments can provide a probe wherein fewer materials can be used, including using less costly materials and represents a substantial improvement over existing differential pH probes.

The ionic probe according to some embodiments provides electrodes that are glass-encased, providing less internal electrolyte contamination, a longer life, a lower operating cost, and requiring less maintenance.

The ionic probe according to some embodiments is very compact. An ionic probe according to the invention can be incorporated into other devices or meters and can be employed with a minimum of space required.

Figure 11:
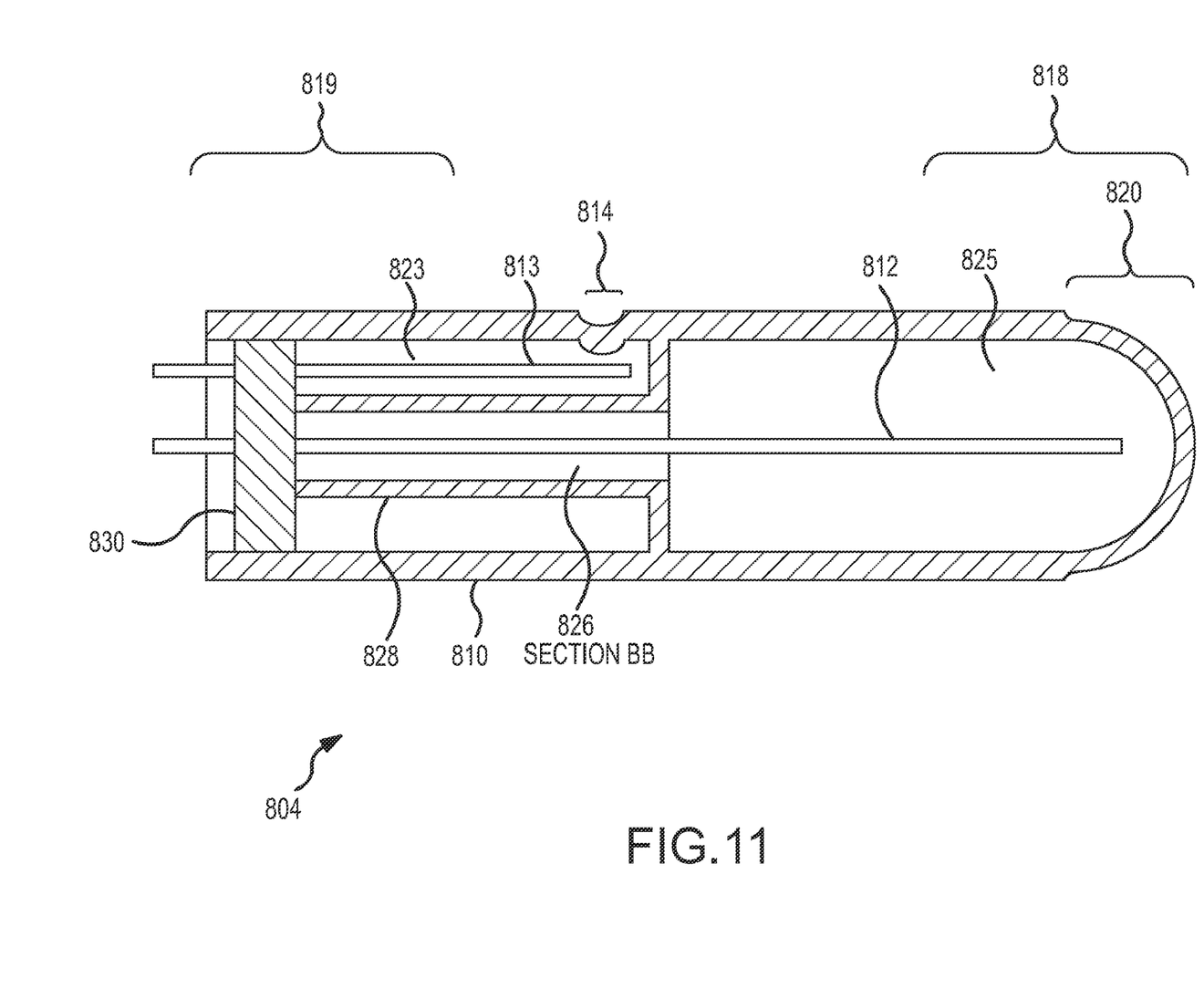
FIG. 11 is a longitudinal cross-sectional view BB of the ionic probe according to an embodiment of the invention.

FIG. 11 is a longitudinal cross-sectional view BB of the ionic probe 804 according to an embodiment of the invention. In this embodiment, only a single seal 830 is required. The single seal 830 blocks off both the reference chamber 823 and the tube 826.

Figure 12:
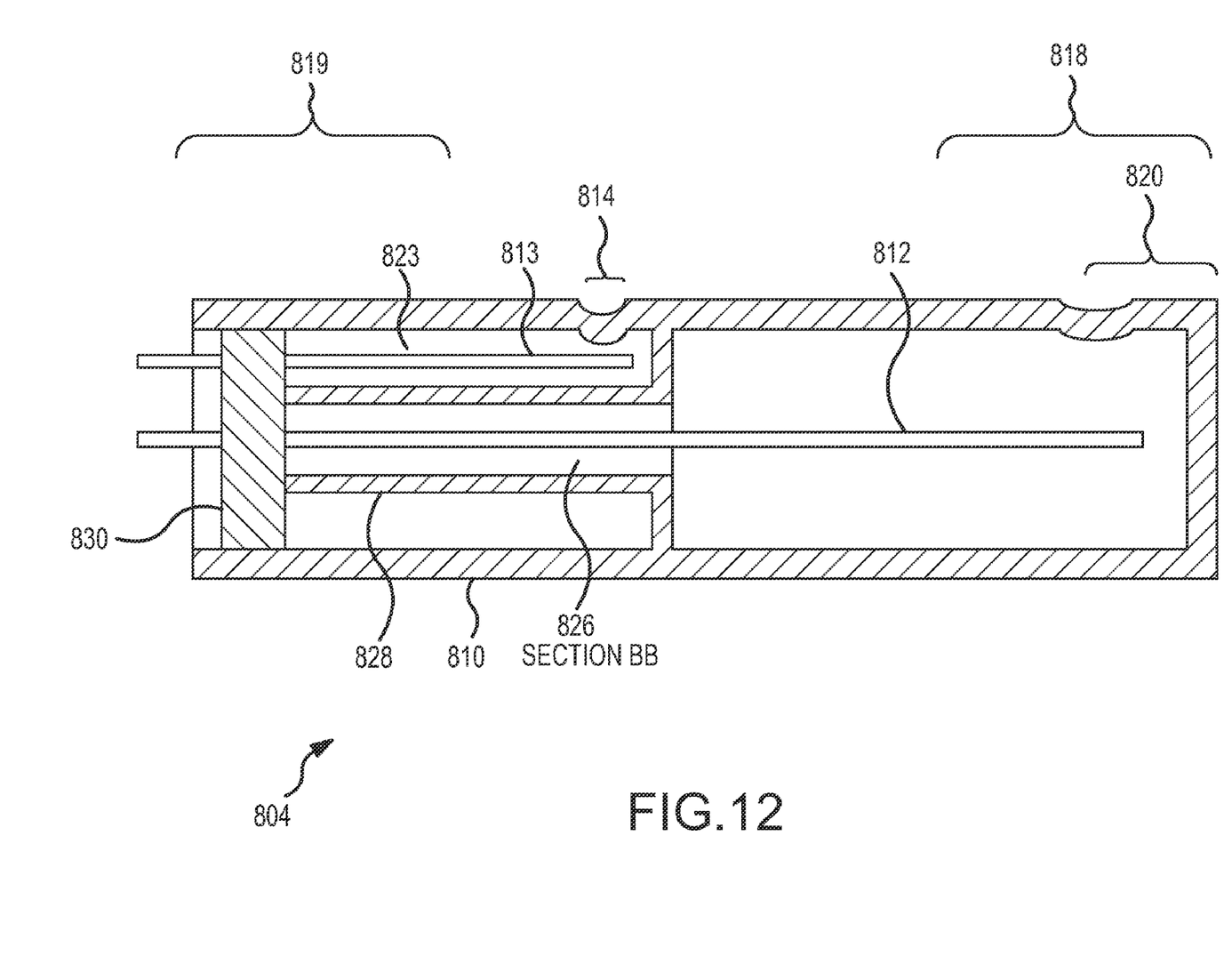
FIG. 12 is a longitudinal cross-sectional view BB of the ionic probe according to an embodiment of the invention.

FIG. 12 is a longitudinal cross-sectional view BB of the ionic probe 804 according to an embodiment of the invention. In this embodiment, the active ion sensitive region 820 is formed on a side of the ionic probe 804, at or near the proximal end 818. As previously discussed, the active ion sensitive region 820 can be formed in the elongate body 810 in any manner, including melting or gluing the active ion sensitive region 820 into an aperture in the elongate body 810. In this embodiment, the active ion sensitive region 820 can extend partially or fully around a circumference of the elongate body 810 and can extend any desired distance toward the distal end 819. In contrast to the embodiments of FIGS. 10 and 11, the active ion sensitive region 820 is not located coaxially or radially at the proximal end 818 and/or with respect to the axis AA. As a result, the active ion sensitive region 820 is less exposed to contact and less likely to be impacted or damaged.

We claim:
1. A unitary ionic probe, comprising:
a substantially elongate body including a central axis, a proximal end, and a distal end;
an active ion sensitive region of pH glass that is located on and bonded into an exterior of the elongate body in a region of the proximal end;

an active electrode in ionic communication with the active ion sensitive region;

a reference ion sensitive region of pH glass that is located on and bonded into the exterior of the elongate body and is spaced-apart from the active ion sensitive region; and a reference electrode in ionic communication with the reference ion sensitive region.

2. The unitary ionic probe of claim 1, wherein the active ion sensitive region extends substantially radially from the proximal end and wherein the reference ion sensitive region is located on a circumferential outer surface of the elongate body.

3. The unitary ionic probe of claim 2, wherein the active ion sensitive region is substantially planar in shape.

4. The unitary ionic probe of claim 2, wherein the active ion sensitive region is substantially domed in shape.

5. The unitary ionic probe of claim 1, wherein the active ion sensitive region is located on a circumferential outer surface of the elongate body at the proximal end and wherein the reference ion sensitive region is located on the circumferential outer surface and spaced-apart from the active ion sensitive region.

6. The unitary ionic probe of claim 1, with the active ion sensitive region comprising a first portion of ion-sensitive material bonded into the elongate body and with the reference ion sensitive region comprising a second portion of ion-sensitive material bonded into the elongate body.

7. The unitary ionic probe of claim 1, with the ionic probe being substantially cylindrical and further comprising an inner wall forming a reference chamber located at the distal end, with the reference chamber holding the reference electrode and being in communication with the reference ion sensitive region.

8. The unitary ionic probe of claim 1, with the ionic probe being substantially cylindrical and further comprising a substantially annular inner wall forming a substantially annular reference chamber located at the distal end, with the reference chamber holding the reference electrode and being in communication with the reference ion sensitive region.

9. The unitary ionic probe of claim 1, with the ionic probe being substantially cylindrical and further comprising a substantially annular inner wall forming a substantially annular reference chamber located at the distal end, with the reference chamber holding the reference electrode and being in communication with the reference ion sensitive region, wherein the inner wall is substantially coaxial with the central axis.

10. The unitary ionic probe of claim 1, further comprising one or more seals sealing the distal end of the elongate body, with the one or more seal allowing the active electrode and the reference electrode to exit the elongate body.

11. The unitary ionic probe of claim 1, further comprising a single seal sealing the distal end of the elongate body, with the seal allowing the active electrode and the reference electrode to exit the elongate body.

12. A unitary ionic probe, comprising:

a substantially elongate body including a central axis, a proximal end, and a distal end;

an active ion sensitive region of pH glass that is located on and bonded into an exterior of the elongate body in a region of the proximal end, wherein the active ion sensitive region extends substantially radially from the proximal end;

an active electrode in ionic communication with the active ion sensitive region;

a reference ion sensitive region of pH glass that is located on and bonded into a circumferential outer surface and is spaced-apart from the active ion sensitive region; and a reference electrode in ionic communication with the reference ion sensitive region.

13. The unitary ionic probe of claim 12, wherein the active ion sensitive region is substantially planar in shape.

14. The unitary ionic probe of claim 12, wherein the active ion sensitive region is substantially domed in shape.

15. The unitary ionic probe of claim 12, with the active ion sensitive region comprising a first portion of ion-sensitive material bonded into the elongate body and with the reference ion sensitive region comprising a second portion of ion-sensitive material bonded into the elongate body.

16. The unitary ionic probe of claim 12, with the ionic probe being substantially cylindrical and further comprising an inner wall forming a reference chamber located at the distal end, with the reference chamber holding the reference electrode and being in communication with the reference ion sensitive region.

17. The unitary ionic probe of claim 12, with the ionic probe being substantially cylindrical and further comprising a substantially annular inner wall forming a substantially annular reference chamber located at the distal end, with the reference chamber holding the reference electrode and being in communication with the reference ion sensitive region.

18. The unitary ionic probe of claim 12, with the ionic probe being substantially cylindrical and further comprising a substantially annular inner wall forming a substantially annular reference chamber located at the distal end, with the reference chamber holding the reference electrode and being in communication with the reference ion sensitive region, wherein the inner wall is substantially coaxial with the central axis.

19. The unitary ionic probe of claim 12, further comprising one or more seals sealing the distal end of the elongate body, with the one or more seal allowing the active electrode and the reference electrode to exit the elongate body.

20. The unitary ionic probe of claim 12, further comprising a single seal sealing the distal end of the elongate body, with the seal allowing the active electrode and the reference electrode to exit the elongate body.

21. A unitary ionic probe, comprising:

a substantially elongate body including a central axis, a proximal end, and a distal end;

an active ion sensitive region of pH glass that is located on and bonded into a circumferential outer surface of the elongate body at the proximal end;

an active electrode in ionic communication with the active ion sensitive region;

a reference ion sensitive region of pH glass that is located on and bonded into the circumferential outer surface and spaced-apart from the active ion sensitive region; and a reference electrode in ionic communication with the reference ion sensitive region.

22. The unitary ionic probe of claim 21, with the active ion sensitive region comprising a first portion of ion-sensitive material bonded into the elongate body and with the reference ion sensitive region comprising a second portion of ion-sensitive material bonded into the elongate body.

23. The unitary ionic probe of claim 21, with the ionic probe being substantially cylindrical and further comprising an inner wall forming a reference chamber located at the distal end, with the reference chamber holding the reference electrode and being in communication with the reference ion sensitive region.

24. The unitary ionic probe of claim 21, with the ionic probe being substantially cylindrical and further comprising a substantially annular inner wall forming a substantially annular reference chamber located at the distal end, with the reference chamber holding the reference electrode and being in communication with the reference ion sensitive region.

25. The unitary ionic probe of claim 21, with the ionic probe being substantially cylindrical and further comprising a substantially annular inner wall forming a substantially annular reference chamber located at the distal end, with the reference chamber holding the reference electrode and being in communication with the reference ion sensitive region, wherein the inner wall is substantially coaxial with the central axis.

26. The unitary ionic probe of claim 21, further comprising one or more seals sealing the distal end of the elongate body, with the one or more seals allowing the active electrode and the reference electrode to exit the elongate body.

27. The unitary ionic probe of claim 21, further comprising a single seal sealing the distal end of the elongate body, with the seal allowing the active electrode and the reference electrode to exit the elongate body.

28. A unitary ionic probe, comprising:
a substantially elongate body including a central axis, a proximal end, and a distal end, with the elongate body being substantially cylindrical;
an active ion sensitive region of pH glass bonded into an exterior of the elongate body in a region of the proximal end;
an active electrode in ionic communication with the active ion sensitive region;
a reference ion sensitive region of pH glass bonded into the exterior of the elongate body and spaced-apart from the active ion sensitive region;
a reference electrode in ionic communication with the reference ion sensitive region; and
an inner wall forming a reference chamber located at the distal end, with the reference chamber holding the reference electrode and being in communication with the reference ion sensitive region.

29. The unitary ionic probe of claim 28, wherein the active ion sensitive region extends substantially radially from the proximal end and wherein the reference ion sensitive region is located on a circumferential outer surface of the elongate body.

30. The unitary ionic probe of claim 29, wherein the active ion sensitive region is substantially planar in shape.

31. The unitary ionic probe of claim 29, wherein the active ion sensitive region is substantially domed in shape.

32. The unitary ionic probe of claim 28, wherein the active ion sensitive region is located on a circumferential outer surface of the elongate body at the proximal end and wherein the reference ion sensitive region is located on the circumferential outer surface and spaced-apart from the active ion sensitive region.

33. The unitary ionic probe of claim 28, with the active ion sensitive region comprising a first portion of ion-sensitive material bonded into the elongate body and with the reference ion sensitive region comprising a second portion of ion-sensitive material bonded into the elongate body.

34. The unitary ionic probe of claim 28, with the inner wall and the reference chamber being substantially annular.

35. The unitary ionic probe of claim 28, wherein the inner wall is substantially coaxial with the central axis.

36. The unitary ionic probe of claim 28, further comprising one or more seals sealing the distal end of the elongate body, with the one or more seals allowing the active electrode and the reference electrode to exit the elongate body.

37. The unitary ionic probe of claim 28, further comprising a single seal sealing the distal end of the elongate body, with the seal allowing the active electrode and the reference electrode to exit the elongate body.

38. The unitary ionic probe of claim 1, wherein the substantially elongate body is formed of a piece of glass that includes a contiguous exterior comprising the active ion sensitive region and the reference ion sensitive region.

* * * * *